United States Patent
Narandja et al.

(10) Patent No.: US 6,504,035 B1
(45) Date of Patent: Jan. 7, 2003

(54) 3-DEOXY-DESMYCOSIN DERIVATIVES AND PROCESS FOR THEIR PREPARATION

(75) Inventors: Amalija Narandja, Zagreb (HR); Nevenka Lopotar, Zagreb (HR); Marko Djerek, Zagreb (HR); Dražen Pavlović, Zagreb (HR)

(73) Assignee: PLIVA, farmaceutska industrija, dionicko drustvo, Zagreb (HR)

( * ) Notice: Subject to any disclaimer, the term of this patent is extended or adjusted under 35 U.S.C. 154(b) by 0 days.

(21) Appl. No.: 09/959,692
(22) PCT Filed: May 2, 2000
(86) PCT No.: PCT/HR00/00012
§ 371 (c)(1), (2), (4) Date: Jan. 28, 2002
(87) PCT Pub. No.: WO00/66602
PCT Pub. Date: Nov. 9, 2000

(30) Foreign Application Priority Data

Mar. 5, 1999 (HR) ............................................. P990129A

(51) Int. Cl.$^7$ ..................... C07D 321/00; C07D 305/00
(52) U.S. Cl. ..................... 549/200; 549/263; 549/267; 549/268; 536/2
(58) Field of Search ................................ 549/200, 263, 549/567, 268; 536/6

(56) References Cited

FOREIGN PATENT DOCUMENTS

EP        A-0287082        * 10/1988

OTHER PUBLICATIONS

Kisrt et al, Journal of Antibiotics, vol. 51, No. 7, 1988, pp. 938–948.*

* cited by examiner

*Primary Examiner*—Alan L. Rotman
*Assistant Examiner*—Héctor M. Reyes
(74) *Attorney, Agent, or Firm*—Connolly Bove Lodge & Hutz, LLP

(57) ABSTRACT

The present invention relates to derivatives of 3-deoxy desmycosin of the formula I, wherein, starting from triply protected desmycosin, there are performed an oxidation at C-3 in the first step and then, optionally, a hydrogenation of double bonds and an epoxidation followed by a reductive opening of the oxirane ring. The present invention also relates to derivatives of 3-deoxy-desmycosin of the formula II, wherein in the first step triacetyl desmycosin is hydrogenated and then, via an intermediate mesylate, it is converted to a 2,3-didehydro derivative; or 2,3-didehydro-desmycosin is subjected to epoxidation reactions followed by a reductive opening of the oxirane ring.

18 Claims, No Drawings

3-DEOXY-DESMYCOSIN DERIVATIVES AND PROCESS FOR THEIR PREPARATION

TECHNICAL FIELD

International Patent Classification: A 61 K 31/70, C 07 H 17/08

TECHNICAL PROBLEM

The present invention relates to new tylosin derivatives, new synthetic products of the macrolide class exhibiting antimicrobial activity. It particularly relates to 3-deoxy-3-oxo-desmycosin derivatives of the formula (I)

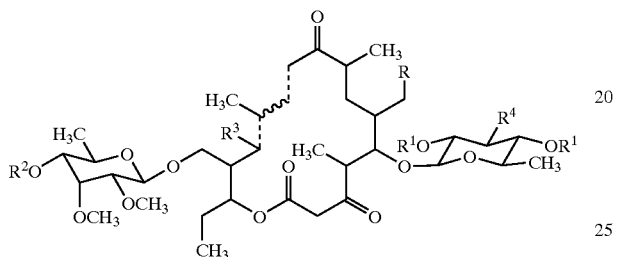

I wherein

R represents CHO or $CH(OCH_3)_2$, $R^1$ and $R^2$ represent H or acetyl, $R^3$ represents H or OH, $R^4$ represents $N(CH_3)_2$ or $N\text{—}O(CH_3)_2$, the line - - - represents a single or a double bond, the line . . . represents $\triangle$ or a double or a single bond, and the line ~~~ represents a double or a single bond, and to derivatives of 3-deoxy-2,3-didehydro-desmycosin of the formula II

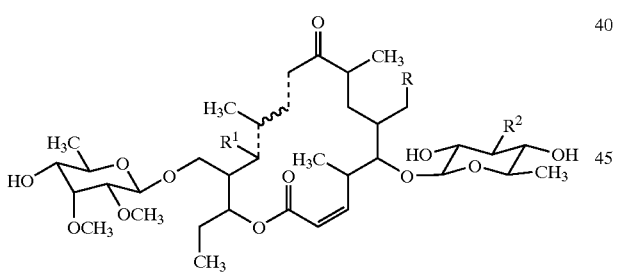

II wherein

R represents CHO or $CH(OCH_3)_2$, $R^1$ represents H or OH, $R^2$ represents $N(CH_3)_2$ or $N\text{—}O(CH_3)_2$, the line - - - represents a double or a single bond, the line . . . represents $\triangle$ or a single bond, and the ~~~ line represents a double or a single bond, and to a process for the preparation thereof.

PRIOR ART

It is known that 13-hydroxy derivatives of tylosin have been prepared by a reductive opening of the oxirane ring (A. Narandja, SI 9700281). It is also known that 10,11,12,13-tetrahydro derivatives of tylosin have been prepared by catalytic hydrogenation of tylosin (A. Narandja, EP 287082 B3). It is also known that 3-deoxy-2,3-didehydro derivatives of tylosin (S. Kageyama, Bull. Chem. Jpn. 65, 3405, 1992) as well as 3-deoxy-3-oxo derivatives of 6-O-methyl-erythromycin (A. Agouridas, J. Med. Chem. 41, 4080, 1998) have been prepared.

According to the known prior art, however, neither 3-deoxy-3oxo-derivatives of tylosin class nor 3-deoxy-2,3-didehydro derivatives with exchanged left side of the molecule in C-10 to C-13 positions and processes for the preparation thereof have been described so far.

TECHNICAL SOLUTION

It has been found that derivatives of 3-deoxy-3-oxo-desmycosin of the formula I

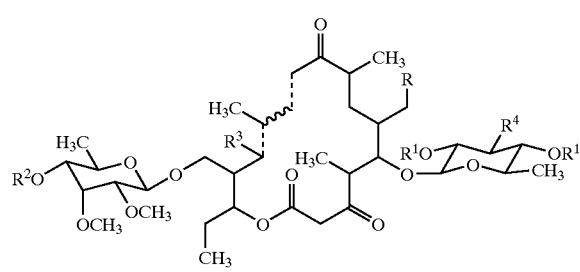

I wherein

R represents CHO or $CH(OCH_3)_2$, $R^1$ and $R^2$ represent H or acetyl, $R^3$ represents H or OH, $R^4$ represents $N(CH_3)_2$ or $N\text{—}O(CH_3)_2$, the line - - - represents a single or a double bond, the line . . . represents $\triangle$ or a double or a single bond, and the line ~~~ represents a double or a single bond, and 3-deoxy-2,3-didehydro-derivatives of the formula II

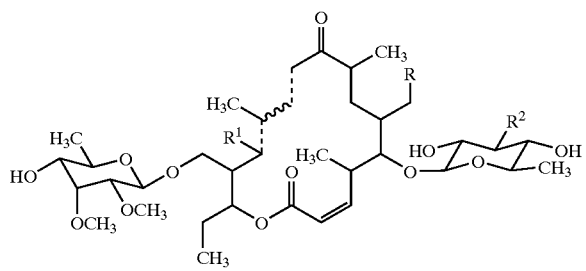

II wherein

R represents CHO or $CH(OCH_3)_2$, $R^1$ represents H or OH, $R^2$ represents $N(CH_3)_2$ or $N\text{—}O(CH_3)_2$, the line - - - represents a double or a single bond, the line . . . represents $\triangle$ or a single bond, and the line ~~~ represents a double or a single bond, can be prepared starting from a compound of the formula III

III

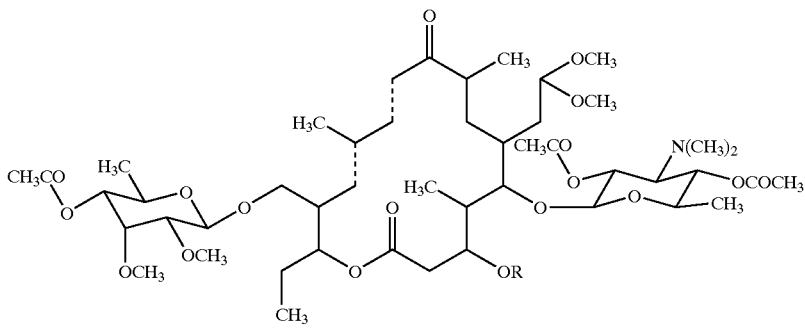

wherein R represents H or $SO_2CH_3$ and the line - - - represents a double or a single bond.

According to the present invention the compound of formula III, wherein R represents H and the line - - - represents a double bond, is subjected A/ to an oxidation reaction in a solution of methylene chloride in the presence of 15–28 equivalents of DMSO, 8–14 equivalents of N-(3-dimethylaminopropyl)-N'-ethyl carbodiimide hydrochloride and 8–14 equivalents of pyridine trifluoroacetate within 2–6 hours at a temperature of 10–25° C., whereupon the obtained compound of the formula I, wherein R represents $CH(OCH_3)_2$, $R^1$ and $R^2$ represent acetyl, $R^3$ represents H, $R^4$ represents $N(CH_3)_2$, the lines - - - and . . . represent double bonds and the line ⁓⁓ represents a single bond, is optionally subjected B/ to a methanolysis at reflux temperature within 4–6 hours and the obtained compound of the formula I, wherein R represents $CH(OCH_3)_2$, $R^1$ and $R^3$ represent H, $R^2$ represents acetyl, $R^4$ represents $N(CH_3)_2$, the lines - - - and . . . represent double bonds and the line ⁓⁓ represents a single bond, is optionally subjected B1/ to an alkaline methanolysis in a mixture of methanol and 25% $NH_4OH$ (2:1) at 5° C. for a period of 48–60 hours, whereupon the obtained compound of the formula I wherein R represents $CH(OCH_3)_2$, $R^1$, $R^2$ and $R^3$ represent H, $R^4$ represents $N(CH_3)_2$, the lines - - - and . . . represent double bonds and the line ⁓⁓ represents a single bond, is optionally subjected B2/ to a hydrolysis in a mixture of acetonitrile and 1% trifluoroacetic acid (2:3) within 2 hours at room temperature, giving a compound of the formula I, wherein R represents CHO, $R^1$, $R^2$ and $R^3$ represent H, $R^4$ represents $N(CH_3)_2$, the lines - - - and . . . represent double bonds and the line ⁓⁓ represents a single bond, or optionally, a compound of the formula I, wherein R represents $CH(OCH_3)_2$, $R^1$ and $R^2$ represent acetyl, $R^3$ represents H and $R^4$ represents $N(CH_3)_2$, the lines - - - and . . . represent double bonds and the line ⁓⁓ represents a single bond, is subjected C/ to a catalytic hydrogenation reaction in the presence of 2–5% Pd/C (w/w) at room temperature within 5–8 hours at a hydrogen pressure of 0.3–0.5 MPa, whereupon the obtained compound of the formula I, wherein R represents $CH(OCH_3)_2$, $R^1$ and $R^2$ represent acetyl, $R^3$ represents H, $R^4$ represents $N(CH_3)_2$, and the lines - - -, . . . and ⁓⁓ represent single bonds, can be optionally subjected to methanolysis or alkaline methanolysis reactions in the manner described under B or B1;

or optionally, it is subjected

D/ to an oxidation reaction in a methylene chloride solution in the presence of 3–6 equivalents of m-chloroperbenzoic acid within 6–10 hours at room temperature, giving a compound of the formula I, wherein R represents $CH(OCH_3)_2$, $R^1$ and $R^2$ represent acetyl, $R^3$ represents H, $R^4$ represents $N—O(CH_3)_2$, the line - - - represents a double bond, the line . . . represents △ and the line ⁓⁓ represents a single bond, or optionally, a compound of the formula I, wherein R represents $CH(OCH_3)_2$, $R^1$ and $R^3$ represent H, $R^2$ represents acetyl, $R^4$ represents $N—(CH_3)_2$, the lines - - - and . . . represent double bonds and the line ⁓⁓ represents a single bond, is subjected to the oxidation reaction in the manner described under D, and the obtained compound of the formula I, wherein R represents $CH(OCH_3)_2$, $R^1$ and $R^3$ represent H, $R^2$ represents acetyl, $R^4$ represents $N—O(CH_3)_2$, the line - - - represents a double bond, the line . . . represents △ and the line ⁓⁓ represents a single bond, is optionally subjected to the catalytic hydrogenation reaction in the manner described under C, giving a compound of the formula I, wherein R represents $CH(OCH_3)_2$, $R^1$ and $R^3$ represent H, $R^2$ represents acetyl, $R^4$ represents $N(CH_3)_2$, the line - - - represents a single bond, the line . . . represents △ and the line ⁓⁓ represents a single bond, is optionally subjected E/ to a reduction reaction with Zn-powder in a solution of EtOH and a 10% aqueous $NH_4OH$ solution (1:2) under maintaining the pH-value of 5.0–5.5, giving a compound of the formula I, wherein R represents $CH(OCH_3)_2$, $R^1$ represents H, $R^2$ represents acetyl, $R^3$ represents OH, $R^4$ represents $N(CH_3)_2$, the lines - - - and . . . represent single bonds and the line ⁓⁓ represents a double bond, or optionally, a compound of the formula I, wherein R represents $CH(OCH_3)_2$, $R^1$, $R^2$ and $R^3$ represent H, $R^4$ represents $N(CH_3)_2$, the lines - - - and . . . represent double bonds and the line ~~~ represents a single bond, is subjected to the oxidation reaction in the manner described under D, and the obtained compound of the formula I, wherein R represents $CH(OCH_3)_2$, $R^1$, $R^2$ and $R^3$ represent H, $R^4$ represents $N—O(CH_3)_2$, the line - - - represents a double bond, the line . . . represents △ and the line ~~~ represents a single bond, is optionally subjected to the catalytic hydrogenation reaction in the manner described under C, giving a compound of the formula I, wherein R represents $CH(OCH_3)_2$, $R^1$, $R^2$ and $R^3$ represent H, $R^4$ represents $N(CH_3)_2$, the line - - - represents a single bond, the line . . . represents △ and the line ~~~ represents a single bond, or optionally, to the reduction with Zn-powder in the manner described under E, giving a compound of the formula I, wherein R represents $CH(OCH_3)_2$, $R^1$ and $R^2$ represent H, $R^3$ represents OH, $R^4$ represents $N(CH_3)_2$, the lines - - - and . . . represent single bonds and the line ~~~ represents a double bond, or optionally, a compound of the formula III, wherein R represents H and the line - - - represents a double bond, is subjected to the catalytic hydrogenation reaction in the manner described under C and the obtained compound of the formula III, wherein R represents H and the line - - - - - represents a single bond, is optionally subjected F/ to a mesylating reaction in a solution of pyridine under the addition of 3–5 equivalents of methanesulfochloride at 10° C. within 3–5 hours and the obtained compound of the formula III, wherein R represents $SO_2CH_3$ and the line - - - represents a single bond, is subjected G/ to a reaction of elimination of mesylate in a mixture of methanol and 25% $NH_4OH$ (2:1) at room temperature within 5 hours and, subsequently, to the methanolysis in the manner described under B1, and the obtained compound of the formula II, wherein R represents $CH(OCH_3)_2$, $R^1$ represents H, $R^2$ represents $N(CH_3)_2$, the lines - - - , . . . and ~~~ represent single bonds, is subjected to the reaction of hydrolysis of acetal in the manner described under B2, or optionally, a compound of the formula II, wherein R represents $CH(OCH_3)_2$, $R^1$ represents H, $R^2$ represents $N(CH_3)_2$, the lines - - - and . . . represent double bonds and the line ~~~ represents a single bond, is subjected to the oxidation reaction in the manner described under D and the obtained compound of the formula II, wherein R represents $CH(OCH_3)_2$, $R^1$ represents H, $R^2$ represents $N—O(CH_3)_2$, the line - - - represents a double bond, the line . . . represents △ and the line ~~~ represents a single bond, is optionally subjected to the reduction reaction in the manner described under E, giving a compound of the formula II, wherein R represents $CH(OCH_3)_2$, $R^1$ represents OH, $R^2$ represents $N(CH_3)_2$, the lines - - - and . . . represent single bonds and the line ~~~ represents a double bond.

According to the present invention the isolation of the products is performed by means of conventional extraction processes from alkaline aqueous solutions by the use of halogenated hydrocarbons such as methylene chloride, chloroform or tetrachloro-methane, followed by evaporation to a dry residue.

The course of the reaction is followed by chromatography on a thin layer of silica gel (Merck 60 $F_{254}$) in solvent systems methylene chloride-methanol-ammonium hydroxide 25% (90:9:1.5, system A), (90:9:0.5, system A1) or methylene chloride-acetone (8:2, system B) (7:3, system C). If appropriate, the separation of the reaction products and the purification of the products for the purpose of spectral analyses are performed on a silica gel column (Merck 60, 230–400 mesh/ASTM, or 60–230 mesh/ASTM in solvent systems A, B or C). The identification of the novel compounds is performed by UV and NMR spectroscopies and by mass analysis.

The novel compounds show antibacterial activity, however, they can also be used as intermediates for the preparation of new derivatives.

The present invention is illustrated but in no way limited by the following Examples.

Preparation of 2',4'-diacetyl-desmycosin 20-dimethylacetal

Desmycosin 20-dimethylacetal (20 g, 24.4 mmol) was dissolved in methylene chloride (100 ml), acetanhydride (7.2 ml, 76.2 mmol) was added thereto and it was stirred at room temperature for 1 hour. The reaction mixture was poured into 400 ml of water, alkalized to a pH value of 8.5 and subsequently, after the removal of the organic layer, extracted once more with methylene chloride. The combined extracts were washed with a saturated $NaHCO_3$ solution, dried and evaporated to a dry residue.

Obtained: 19.6 g, 89.0%; Rf (A) 0.68; Rf (B) 0.45; $MH^+$ 902.

Preparation of 2',4',4"-triacetyl-desmycosin 20-dimethylacetal

2',4'-diacetyl-desmycosin 20-dimethylacetal (19.6 g, 21.7 mmol) was dissolved in methylene chloride (700 ml) and 4-(dimethylamino)pyridine (0.54 g, 3.7 mmol), triethylamine (27 ml) and acetanhydride (2.7 ml, 28.5 mmol) were added thereto. The reaction mixture was stirred at room temperature for 2 hours, poured into 1000 ml of water and, after the removal of the organic layer, it was extracted once more with methylene chloride. The combined extracts were dried and evaporated to a dry residue.

Obtained: 19.5 g, 95.1%; Rf (A) 0.90; Rf (B) 0.60; $MH^+$ 944.

Preparation of 3-methansuffonyl-2',4',4"-triacetyl-desmycosin 20-dimethylacetal

2',4',4"-triacetyl-desmycosin 20-dimethylacetal (3 g, 3.18 mmol) was dissolved in pyridine (9.5 ml) and it was cooled to 10° C., whereupon methanesulfochloride (1.57 ml, 12.4 mmol) was gradually added thereto. The reaction solution was stirred for 3 hours at 10° C., whereupon it was poured into 250 ml of water, alkalized to a pH value of 9.2 and kept under stirring for 30 minutes. A thick white precipitate was separated by filtration and the still moist precipitate was dissolved in chloroform (60 ml) and washed with a saturated NaCl solution (120 ml). The extract was dried and evaporated to a dry residue.

Obtained: 3.05 g, 94.1%; Rf (A) 0.95; Rf (B) 0.70; $MH^+$ 1022.

Preparation of 2,3-anhydro-desmycosin 20-dimethylacetal 3-methanesulfonyl-2',4',4"-triacetyl-desmycosin 20-dimethylacetal (3 g, 2.9 mmol) was dissolved in methanol (60 ml), 25% $NH_4OH$ (30 ml) was added thereto and it was stirred at room temperature for 3 hours. The reaction mixture was evaporated to ⅓ of its volume under reduced pressure, extracted with chloroform, dried and evaporated to a dry residue. The crude product was dissolved in methanol (160 ml) and heated at reflux temperature for 6 hours, whereupon methanol was evaporated and the product was dissolved in chloroform (150 ml), washed with a saturated NaHCO$_3$ solution and evaporated to a dry residue.

Obtained: 2.22 g, 94.4%; Rf (A) 0.50; MH$^+$ 800.

EXAMPLE 1

3-deoxy-3-oxo-2',4',4"-triacetyl-desmycosin 20-dimethylacetal (1)

2',4',4"-triacetyl-desmycosin 20-dimethylacetal (10 g, 0.01 mmol) was dissolved in methylene chloride (230 ml), dimethylsulfoxide (16 ml, 0.22 mol) and, subsequently, N(3-dimethylaminopropyl)-N'-ethyl carbodiimide hydrochloride (20 g, 0.1 mol) were added thereto and the reaction mixture was cooled to 10° C. A solution of pyridine trifluoroacetate (20.2 g, 0.1 mol) in methylene chloride (115 ml) was added dropweise within 30 minutes. After 4 hours of stirring at room temperature the reaction solution was poured into 850 ml of water and the organic layer was separated and extracted once more with methylene chloride. The combined extracts were washed with a saturated NaCl solution and evaporated to a dry residue.

Obtained: 9.73 g, 97.6%; Rf (A) 0.95, Rf (C) 0.65; MH$^+$ 942; UV$_{\lambda max.}$ 282 nm, ε18900.

By chromatography on a silica gel column in the solvent system C, a product with the following characteristics demonstrating a product proportionated with its enol form (in proportion 1:1; determined according to the intensity of the characteristic signals) was obtained:

$^1$H-NMR (CDCl$_3$) δ ppm: 12.04 (1H, s, 3-OH, enol, interchangeable with D$_2$O), 7.14, 7.06 (1H, d, H-11), 6.25, 6.02 (1H, d, H-10), 5.82, 5.75 (1H, d, H-13), 4.89 (1H, dd, H-2), 4.74 (1H, dd, H-4'), 4.72 (1H, s, H-2, enol), 4.65 (1H, d, H-1"), 4.44 (1H, dd, H-4"), 4.38 (1H, d, H-1'), 3.53 (3H, s, 3"-OMe), 3.47 (3H, s, 2"-OMe), 3.34 (3H, s, 20-OMe), 3.29 (3H, s, 20-OMe), 2.34 (6H, s, NMe$_2$), 2.12 (3H, s, COMe), 2.06 (6H, s, 2×COMe), 1.88 (3H, s, H-22).

$^{13}$C-NMR (CDCl$_3$) δ ppm: 205.5 (s, C-3, keto), 205.2, 203.9 (s, C-9), 180.2 (s, C-3, enol), 172.9, 166.6 (s, C-1), 170.4, 170.1, 169.6 (s, 3×COMe, 147.6, 146.5 (d, C-11), 140.5, 139.0 (d, C-13), 137.6, 136.8 (s, C-12), 124.2, 119.6 (d, C-10), 88.9 (d, C-2, enol), 46.5 (t, C-2, keto), 20.9, 20.8, 20.6 (q, 3×COMe).

EXAMPLE 2

3-deoxy-3-oxo-4"-acetyl-desmycosin 20-dimethylacetal (2)

Compound 1 (9 g, 9,6 mmol) was dissolved in methanol (180 ml) and heated at reflux temperature for 4 hours, whereupon the reaction solution was evaporated to dryness and the product was dissolved in chloroform (90 ml) and washed with a saturated NaHCO$_3$ solution. The extract was dried and evaporated to a dry residue.

Obtained: 8.1 g, 98%; Rf (A) 0.45; MH$^+$ 858.

By chromatography on a silica gel column in the alkali solvent system A, the keto-enol proportion was shifted in favour of the keto form (3:1).

$^1$H-NMR (DMSO-d$_6$) δ ppm: 12.00 (1H, s, 3-OH, interchangeable with D$_2$O), 6.99, 6.94 (1H, d, H-11), 6.47 (1H, d, H-10), 5.80, 5.68 (1H, d, H-13), 4.75 (1H, s, H-2, enol), 4.64 (1H, d, H-1"), 4.41 (1H, dd, H-4"), 4.38 (1H, d, H-1'), 3.39 (3H, s, 3"-OMe), 3.34 (3H, s, 2"-OMe), 3.25 (3H, s, 20-OMe), 3.22 (3H, s, 20-OMe), 2.40 (6H, s, NMe$_2$), 2.08 (3H, s, COMe), 1.81, 1.79 (3H, s, H-22).

$^{13}$C-NMR (CDCl$_3$) δ ppm: 205.6 (s, C-3, keto), 205.4, 203.9 (s, C-9), 180.1 (s, C-3, enol), 172.5, 166.8 (s, C-1), 170.4 (s, COMe), 147.6. 146.8 (D, C-11), 140.5, 139.01 (d, C-13), 136.8, 134.3 (s, C-12), 124.3, 119.8 (d, C-10), 46.3 (t, C-2), 20.5 (q, COMe).

EXAMPLE 3

3-deoxy-3-oxo-desmycosin 20-dimethylacetal (3)

Compound 2 (3.2 g, 3.72 mmol) was dissolved in methanol (64 ml), 25% NH$_4$OH (32 ml) was added and it was left to stand at 5° C. for a period of 60 hours. The reaction solution was evaporated to an oily product, which was dissolved in chloroform (60 ml), washed with a saturated NaHCO$_3$ solution and evaporated to a dry residue.

Obtained: 2.25 g, 74.0%; Rf (A) 0.38; MH$^+$ 816.

By chromatography on a silica gel column in the solvent system A, a product with the following characteristics was obtained:

$^1$H-NMR (CDCl$_3$) δ ppm: 7.16, 7.08 (1H, d, H-11), 6.25, 6.02 (1H, d, H-10), 5.81, 5.74 (1H, d, H-13), 4.74 (1H, s, H-2, enol), 4.64 (1H, d, H-1"), 4.38 (1H, d, H-1'), 3.53 (3H, s, 3"-OMe), 3.47 (3H, s, 2"-OMe), 3.29 (3H, s, 20-OMe), 3.22, (3H, s, 20-OMe), 2.34 (6H, s, NMe$_2$), 1.78 (3H, s, H-22).

EXAMPLE 4

3-deoxy-3-oxo-desmycosin (4)

Compound 3 (1 g, 1.22 mmol) was dissolved in acetonitrile (10 ml) and 1% trifluoroacetic acid (12 ml), stirred for 2 hours at room temperature, chloroform (7 ml) was added thereto and it was alkalized to a pH value of 8.5. The organic layer was separated, extracted once more with chloroform and the combined extracts were dried and evaporated to a dry residue.

Obtained: 0.79 g, 84.0%; Rf (A) 0.32; MH$^+$ 770.

By chromatography on a silica gel column in the solvent system A, a product with the characteristics of a keto form was isolated.

$^1$H-NMR (CDCl$_3$) δ ppm: 9.72 (1H, s, H-20), 7.30 (1H, d, H-11), 6.04 (1H, d, H-10), 5.95 (1H, d, H-13), 4.64 (1H, d, H-1"), 4.38 (1H, d, H-1"), 3.53 (3H, s, 3"-OMe), 3.47 (3H, s, 2"-OMe), 2.34 (6H, s, NMe$_2$), 1.78 (3H, s, H-22).

EXAMPLE 5

2',4',4"-triacetyl-10,11,12,13-tetrahydro-desmycosin 20-dimethylacetal (5)

2',4',4"-triacetyl-desmycosin 20-dimethylacetal (6 g, 6.3 mmol) was dissolved in ethanol (250 ml), 3 g of 10% Pd/C (w/w) were added thereto and it was hydrogenated for 7 hours at room temperature and at a hydrogen pressure of 0.5 MPa. After the completion of the reaction the catalyst was separated by filtration and ethanol was evaporated under reduced pressure to a dry residue.

Obtained: 5.8 g, 96.3%; Rf (A) 0.88; Rf (B) 0.45; MH$^+$ 948; (does not adsorb in UV spectrum).

By chromatography on a silica gel column in the solvent system B, a product with the following characteristics was obtained:

$^1$H-NMR (CDCl$_3$) δ ppm: 4.89 (1H, dd, H-2'), 4.74 (1H, dd, H-4'), 4.58 (1H, d, H-1"), 4.44 (1H, dd, H-4"), 4.38 (1H, d, H-1'), 3.53 (3H, s, 3"-OMe), 3.47 (3H, s, 2"-OMe), 3.29 (3H, s, 20-OMe), 3.22, (3H, s, 20-OMe), 2.34 (6H, s, NMe$_2$), 2.12 (3H, s, COMe), 2.06 (6H, s 2×COMe), 0.94 (3H, d, H-22).

$^{13}$C-NMR (CDCl$_3$) δ ppm: 214.8, (s, C-9), 172.0, (s, C-1), 170.0, 169.7, 169.1 (s, 3×<u>C</u>OMe), 39.2 (t, C-13), 34.8 (t, C-10), 29.7 (d, C-12), 29.4 (t, C-11), 20.8, 20.7, 20.06(q, 3×CO<u>Me</u>).

EXAMPLE 6

3-deoxy-3-oxo-2',4',4"-triacetyl-10,11,12,13-tetrahydro-desmycosin 20-dimethylacetal (6)

Process A

Compound 5 (5 g, 5.3 mmol) was dissolved in methylene chloride (120 ml), dimethylsulfoxide (8 ml, 0.11 mol) and, subsequently, N(3-dimethylaminopropyl)-N'-ethyl carbodiimide hydrochloride (10 g, 50 mmol) were added thereto and the reaction mixture was cooled to 10° C. A solution of pyridine trifluoroacetate (10.2 g, 50 mmol) in methylene chloride (60 ml) was added dropwise within 30 minutes. After 4 hours of stirring at room temperature the reaction solution was poured into 430 ml of water and the organic layer was separated and extracted once more with methylene chloride. The combined extracts were washed with a saturated NaCl solution and evaporated to a dry residue.

Obtained: 4.75 g, 95.2%; Rf (A) 0.93, Rf (B) 0.60; MH$^+$ 946; (does not adsorb in UV spectrum).

By chromatography on a silica gel column in the solvent system B, a keto-enol product (proportion 3:1 in favour of the keto form) with the following characteristics was obtained:

$^{13}$C-NMR (CDCl$_3$) δ ppm: 216.4, 215.1 (s, C-9), 205.9 (s, C-3, keto), 178.2 (s, C-3, enol), 172.4, 166.7 (s, C-1), 170.0, 169.7, 169.1 (s, 3×<u>C</u>OMe), 48.0 (t, C-2, keto), 39.6 (t, C-13), 33.8 (t, C-10), 29.9 (d, C-12), 29.4 (t, C-11), 20.8, 20.7, 20.6 (q, 3×CO<u>Me</u>).

EXAMPLE 7

3-deoxy-3-oxo-4"-acetyl-10,11,12,13-tetrahydro-desmycosin 20-dimethylacetal (7)

Process A

Compound 6 (9 g, 9.5 mmol) was dissolved in methanol (180 ml) and heated at reflux temperature for 4 hours, whereupon the reaction mixture was evaporated to dryness and the product was dissolved in chloroform (90 ml) and washed with a saturated NaHCO$_3$ solution. The extract was dried and evaporated to a dry residue.

Obtained: 7.7 g, 93.9%; Rf (A) 0.42; MH$^+$ 862; (does not adsorb in UV spectrum).

By chromatography on a silica gel column in the solvent system A, a keto-enol product (proportion 3:1 in favour of the keto form) with the following characteristics was obtained:

$^{13}$C-NMR (CDCl$_3$) δ ppm: 216.6, 215.1 (s, C-9), 205.9 (s, C-3, keto), 178.2 (s, C-3, enol), 172.4, 166.7 (s, C-1), 169.7, (s, <u>C</u>OMe), 48.0 (t, C-2, keto), 39.6 (t, C-13), 33.8 (t, C-10), 29.9 (d, C-12), 29.4 (t, C-11), 20.8, 20.7, 20.6 (q, 3×CO<u>Me</u>).

Process B

Compound 2 (6 g, 6.97 mmol) was dissolved in ethanol (250 ml), 3 g of 10% Pd/C (w/w) were added and it was hydrogenated for 6 hours at room temperature and at a hydrogen pressure of 0.5 MPa. After the completion of the reaction the catalyst was separated by filtration and ethanol was evaporated at a reduced pressure to a dry residue.

Obtained: 5.7 g, 95.0%.

By chromatography on a silica gel column in the solvent system A, a product with the same characteristics as the product obtained by process A was obtained.

EXAMPLE 8

3-deoxy-3-oxo-10,11,12,13-tetrahydro-desmycosin 20-dimethylacetal (8)

Process A

Compound 7 (3.0 g, 3.48 mmol) was dissolved in methanol (60 ml), 25% NH$_4$OH (30 ml) was added thereto and it was left to stand at 5° C. for a period of 60 hours. The reaction solution was evaporated and processed in the manner described in Example 3.

Obtained: 2.08 g, 73.0%; Rf (A) 0.35; MH$^+$ 820.

By chromatography on a silica gel column in the solvent system A, a product with the following characteristics was obtained:

$^1$H-NMR (CDCl$_3$) δ ppm 4.58 (1H, d, H-1"), 4.38 (1H, d, H-1'), 3.53 (3H, s,3"-OMe), 3.47 (3H, s, 2"-OMe), 3.29 (3H, s, 20-OMe), 3.22, (3H, s, 20-OMe), 2.34 (6H, s, NMe$_2$), 0.95 (3H, d, H-22).

$^{13}$C-NMR (CDCl$_3$) δ ppm: 215.8 (s, C-9), 206.7 (s, C-3), 166.7 (s, C-1), 45.8 (t, C-2), 39.4 (t, C-13), 34.8 (t, C-10), 29.7 (d, C-12), 29.4 (t, C-11).

Process B

Compound 3 (6 g, 7.35 mmol) was dissolved in ethanol (250 ml), 3 g of 10% Pd/C (w/w) were added thereto and it was hydrogenated for 7 hours at room temperature at hydrogen pressure of 0.5 MPa. After the completion of the reaction the catalyst was separated by filtration and ethanol was evaporated at a reduced pressure to a dry residue.

Obtained: 5.8 g, 96.2%.

By chromatography on a silica gel column in the solvent system A1, a product with the same characteristics as the product obtained by process A was obtained.

EXAMPLE 9

12,13-epoxy-3-deoxy-3-oxo-2',4'4"-triacetyl-desmycosin (3'N-oxide) 20-dimethylacetal (9)

Compound 1 (2 g, 2.12 mmol) was dissolved in methylene chloride (40 ml), 71% m-chloroperbenzoic acid (2.05 g, 8.4 mmol) was added and it was stirred at room temperature for 8 hours. The reaction mixture was poured into 80 ml of water, alkalized to a pH value of 8.6, stirred for 30 minutes and the organic layer was separated. Subsequently, it was extracted once more with methylene chloride. The combined extracts were dried and evaporated to a dry residue.

Obtained: 1.91 g, 94.0%; Rf (A) 0.23; MH$^+$ 974; UV$_{\lambda max}$ 238 nm, ϵ14597.

By chromatography on a silica gel column in the solvent system A, a keto-enol product (proportion 3:1 in favour of the keto form) with the following characteristics was obtained:

$^1$H-NMR (CDCl$_3$) δ ppm: 11.91 (1H, s, 3-OH, interchangeable with D$_2$O), 6.57, 6.55 (1H, d, H-11), 6.43, 6.41 (1H, d, H-10), 4.91 (1H, dd, H-2'), 4.78 (1H, dd, H-4'), 4.64 (1H, d, H-1"), 4.45 (1H, dd, H-4"), 4.13 (1H, d, H-1'), 3.59 (3H, s, 3"-OMe), 3,46 (6H, s, N-Me, 2"-OMe), 3.31 (3H, s, 20-OMe), 3.29, (3H, s, 20-OMe), 3.25 (3H, s, NMe), 2.12 (9H, s, 3×COMe), 1.44 (3H, s, H-22).

$^{13}$C-NMR (CDCl$_3$) δ ppm: 205.7 (s, C-3, keto), 200.8 (s, C-9), 179.2 (s, C-3, enol), 175.3, 166.2 (s, C-1), 171.6, 170.3, 170.1 (s, 3×<u>C</u>OMe) 150.4, 147.3 (d, C-11), 124.2, 123.3 (d, C-10), 62.9 (s, C-12), 48.3 (t, C-2).

EXAMPLE 10

12,13-epoxy-3-deoxy-3-oxo-4"-acetyl-desmycosin (3'N-oxide) 20-dimethylacetal (10)

Compound 2 (3 g, 3.5 mmol) was dissolved in methylene chloride (60 ml), 71% m-chloroperbenzoic acid (3.35 g, 14.0 mmol) was added thereto and it was stirred at room temperature for 8 hours. The product was isolated from the reaction solution as described in Example 9.

Obtained: 2.64 g, 85%; Rf (A) 0.22; MH$^+$ 890; UV$_{\lambda max.}$ 238 nm, $\epsilon$15297.

By chromatography on a silica gel column in the solvent system A, a keto-enol product (proportion 3:1 in favour of the keto form) with the following characteristics was obtained:

$^1$H-NMR (CDCl$_3$) $\delta$ ppm 11.91 (1H, s, 3-OH, interchangeable with D$_2$O), 6.57, 6.55 (1H, d, H-11), 6.43, 6.41 (1H, d, H-10), 4.64 (1H, d, H-1"), 4.44 (1H, dd, H-4"), 4.42 (1H, d, H-1'), 3.59 (3H, s, 3"-OMe), 3.46 (6H, s, N-Me, 2"-OMe), 3.31 (3H, s, 20-OMe), 3.29, (3H, s, 20-OMe), 3.25 (3H, s, NMe), 2.12. (3H, s, COMe), 1.51 (3H, s, H-22).

$^{13}$C-NMR (CDCl$_3$) $\delta$ ppm: 205.7 (s, C-3, keto), 200.8 (s, C-9), 179.2 (s, C-3, enol), 175.3, 166.2 (s, C-1), 170.1, (s, COMe), 150.4, 147.3 (d, C-11), 124.2, 123.3 (d, C-10), 62.9 (s, C-12), 48.3 (t, C-2).

EXAMPLE 11

12,13-epoxy-3-deoxy-3-oxo-desmycosin (3'N-oxide) 20-dimethylacetal (11)

Compound 3 (2 g, 2.45 mmol) was dissolved in methylene chloride (40 ml), 71% m-chloroperbenzoic acid (2.37 g, 9.8 mmol) was added thereto, whereupon the reaction and isolation in the manner described in Example 9 were performed.

Obtained: 1.64 g, 79%; Rf (A) 0.22; MH$^+$ 848.

By chromatography on a silica gel column in the solvent system A, a keto-enol product (proportion 3:1 in favour of the keto form) with the following characteristics was obtained:

$^1$H-NMR (CDCl$_3$) $\delta$ ppm 11.91 (1H, s, 3-OH, interchangeable with D$_2$O), 6.56, 6.53 (1H, d, H-11), 6.41, 6.40 (1H, d, H-10), 4.64 (1H, d, H-1"), 4.42 (1H, d, H-1'), 3.59 (3H, s, 3"-OMe), 3.46 (6H, s, N-Me, 2"-OMe), 3.31 (3 H, s, 20-OMe), 3.29, (3H, s, 20-OMe), 3.25 (3H, s, NMe), 1.51 (3H, s, H-22).

EXAMPLE 12

10,11-dihydro-12,13-epoxy-3-deoxy-3-oxo-desmycosin 20-dimethylacetal (12)

Compound 11 (1 g, 1.18 mmol) was dissolved in ethanol (50 ml), 0.33 g of 10% Pd/C (w/w) were added thereto, whereupon the hydrogenation in the manner described in Example 5 was performed.

Obtained: 0.95 g, 96.9%; Rf (A) 0.50; MH$^+$ 834; (does not adsorb in UV-spectrum).

By chromatography on a silica gel column in the solvent system A, a product with the following characteristics was obtained:

$^1$H-NMR (CDCl$_3$) $\delta$ ppm 4.64 (1H, d, H-1"), 4.38 (1H, d, H-1'), 3.59 (3H, s, 3"-OMe), 3.46 (3H, s, 2"-OMe), 3.31 (3H, s, 20-OMe), 3.29, (3H, s, 20-OMe), 2.50 (6H, s, NMe$_2$), 1.34 (3H, s, H-22).

EXAMPLE 13

10,13-dihydro-13-hidroxy-3-deoxy-3-oxo-4"-acetyl-desmycosin 20-dimethylacetal (13)

Compound 10 (1 g, 1.12 mmol) was dissolved in ethanol (20 ml), a 10% aqueous NH$_4$Cl solution (40 ml) and, gradually, Zn-powder (2 g) were added thereto. It was stirred at room temperature for 6 hours, whereupon Zn was removed by filtration and the reaction solution was evaporated to ½ of its volume, chloroform (20 ml) was added and it was alkalized to a pH value of 8.5. The organic layer was separated and another extraction with chloroform was performed. The combined extracts were dried and evaporated to a dry residue.

Obtained: 0.64 g, 65%; Rf (A) 0.45; MH$^+$ 876.

By chromatography on a silica gel column in the solvent system A, a keto-enol product (1:1) with the following characteristics was obtained:

$^1$H-NMR (CDCl$_3$) $\delta$ ppm 12.04 (1H, s, 3-OH, enol, interchangeable with D$_2$O), 5.38, 5.30 (1H, t, H-11), 4.78 (1H, s, H-2, enol), 4.49 (1H, d, H-1"), 4.38 (1H, d, H-1'), 4.30 (1H, dd, H-4"), 3.59 (3H, s, 3"-OMe), 3.46 (3H, s, 2"-OMe), 3.31 (3H, s, 20 -OMe), 3.29 (3H, s, 20 -OMe), 2.39 (6H, s, NMe$_2$), 2.12 (3H, s, COMe), 1.49 (3H, s, H-22).

EXAMPLE 14

2,3-anhydro-12,13-epoxy-desmycosin (3'N-oxide) 20-dimethylacetal (14)

2,3-anhydro-desmycosin 20-dimethylacetal (4 g, 5.00 mmol) was dissolved in methylene chloride (80 ml), 71% m-chloroperbenzoic acid (4.84 g, 0.02 mol) was added and then the oxidation in the manner described in Example 9 was performed.

Obtained: 2.83 g, 68%; Rf (A) 0.20; MH$^+$ 832; UV$_{\lambda max.}$ 238 nm, $\epsilon$12247.

By chromatography on a silica gel column in the solvent system A, a product with the following characteristics was obtained:

$^1$H-NMR (CDCl$_3$) $\delta$ ppm 6.66 (1H, m, H-3), 6.53 (1H, d, H-11), 6.36 (1H, d, 10), 5.75 (1H, d, H-2), 4.58 (1H, d, H-1"), 4.41 (1H, d, H-1'), 3.59 (3H, s, 3"-OMe), 3.46 (6H, s, N-Me, 2"-OMe), 3.31 (3H, s, 20-OMe), 3.29, (3H, s, 20-OMe), 3.25 (3H, s, N-Me), 1.50 (3H, s, H-22).

EXAMPLE 15

2,3-anhydro-10,13-dihydro-13-hydroxy-desmycosin 20-dimethylacetal (15)

Compound 14 (1 g, 1.20 mmol) was dissolved in ethanol (12 ml), a 10% NH$_4$OH solution (24 ml) and, gradually, Zn-powder (2.5 g) were added thereto. After stirring for 8 hours at room temperature, the isolation in the manner described in Example 14 was performed.

Obtained: 0.95 g, 96.9%; Rf (A) 0.48; MH$^+$ 818; (does not adsorb in UV-spectrum).

$^1$H-NMR (CDCl$_3$) $\delta$ ppm: 6.55 (1H, m, H-3), 5.61 (1H, t, H-11), 5.58 (1H, d, H-2), 4.61 (1H, d, H-1"), 4.32 (1H, d, H-1'), 3.59 (3H, s, 3"-OMe), 3.46 (3H, s, 2"-OMe), 3.31 (3H, s, 20-OMe), 3.29, (3H, s, 20-OMe), 2.51 (6H, s, NMe$_2$), 1.68 (3H, s, H-22).

EXAMPLE 16

3-methanesulfonyl-2',4',4"-triacetyl-10,11,12,13-tetrahydro-desmycosin 20-dimethylacetal (16)

Compound 5 (3 g, 3.16 mmol) was dissolved in pyridine (9.15 ml) and cooled to 10° C., whereupon methanesulfochloride (1.57 ml, 12.4 mmol) was gradually added. The reaction solution was stirred for 3 hours at 10° C., poured into 250 ml of water, alkalized to a pH value of 9.2 and then left to stir for 30 minutes. A thick white precipitate was separated by filtration and the still moist precipitate was dissolved in chloroform (60 ml) and washed with a saturated NaCl solution (120 ml). The extract was dried and evaporated to a dry residue.

Obtained: 2.95 g, 86.5%; Rf (C) 0.70; MH$^+$ 1026; (does not adsorb in UV-spectrum).

By chromatography on a silica gel column in the solvent system C, a product with the following characteristics was obtained:

$^1$H-NMR (CDCl$_3$) δ ppm: 4.89 (1H, dd, H-2'), 4.76 (1H, dd, H-4'), 4.61 (1H, d, H-1"), 4.43 (1H, dd, H-4"), 4.40 (1H, d, H-1'), 3.53 (3H, s, 3"-OMe), 3.47 (3H, s, 2"-OMe), 3.29 (3H, s, 20-OMe), 3.22, (3H, s, 20-OMe), 3.10 (3H, s, SO$_2$Me), 2.34 (6H, s, NMe$_2$), 2.12. (3H, s, COMe), 2.06 (6H, s 2×COMe), 0.96 (3H, d, H-22).

EXAMPLE 17

2,3-anhydro-10,11,12,13-tetrahydro-desmycosin 20-dimethylacetal (17)

Compound 16 (2 g, 1.95 mmol) was dissolved in methanol (40 ml), a 25% NH$_4$OH solution (20 ml) was added thereto and it was stirred at room temperature for 3 hours. The reaction solution was evaporated at a reduced pressure to ⅓ of its volume, extracted with chloroform, dried and evaporated to a dry residue. The crude product was dissolved in methanol (80 ml) and it was heated at reflux temperature for 6 hours. Subsequently, methanol was evaporated and the product was dissolved in chloroform (40 ml), washed with a saturated NaHCO$_3$ solution and evaporated to a dry residue.

Obtained: 1.39 g, 89.0%; Rf (A) 0.45; MH$^+$ 804.

$^1$H-NMR (CDCl$_3$) δ ppm 6.82 (1H, m, H-3), 5.88 (1H, d, H-2), 4.61 (1H, d, H-1"), 4.41 (1H, d, H-1'), 3.59 (3H, s, 3"-OMe), 3.46 (3H, s, 2"-OMe), 3.31 (3H, s, 20 OMe), 3.29 (3H, s, 20-OMe), 2.51 (6H, s, NMe$_2$), 0.76 (3H, s, H-22).

$^{13}$C-NMR (CDCl$_3$) δ ppm: 215.0 (s, C-9), 167.0 (s, C-1), 148.8 (d, C-3), 122.7 (d, C-2), 40.9 (t, C-13), 31.5 (t, C-10), 30.1 (d, C-12), 28.3 (t, C-11), 20.4 (q, C-22).

EXAMPLE 18

2,3-anhydro-10,11,12,13-tetrahydro-desmycosin (18)

Compound 17 (1 g, 1.2 mmol) was dissolved in acetonitrile (10 ml) and in 1% trifluoroacetic acid (13 ml). The reaction solution was stirred for 2 hours at room temperature and then the isolation in the manner described in Example 4 was performed.

Obtained: 0.80 g, 85.0%; Rf (A) 0.35, MH$^+$ 758.

$^1$H-NMR (CDCl$_3$) δ ppm 9.74 (1H, s, H-20), 6.82 (1H, m, H-3), 5.88 (1H, d, H-2), 4.61 (1H, d, H-1"), 4.41 (1H, d, H-1'), 3.59 (3H, s, 3"-OMe), 3.46 (3H, s, 2"-OMe), 2.51 (6H, s, NMe$_2$), 0.76 (3H, s, H-22).

$^{13}$C-NMR (CDCl$_3$) δ ppm: 215.2 (s, C-9), 202.0 (d, C-20), 167.2 (s, C-1), 148.8 (d, C-3), 122.7 (d, C-2), 40.8 (t, C-13), 31.6 (t, C-10), 30.1 (d, C-12), 28.4 (t, C-11), 20.3 (q, C-22).

What is claimed is:

1. Derivatives of 3-deoxy-3-oxo-desmycosin of the formula I wherein
R represents CHO or CH(OCH$_3$)$_2$, R$^1$ and R$^2$ represent H or acetyl, R$^3$ represents H or acetyl, R$^3$ represents H or OH, R$^4$ represents N(CH$_3$)$_2$ or N—O(CH$_3$)$_2$, the line - - - represents a single or a double bond, the line . . . represents △ or a double or a single bond, and the line ∾ represents a double or a single bond, and derivatives of 3-deoxy-2,3-didehydro-desmycosin of the formula II wherein
R represents CHO or CH(OCH$_3$)$_2$, R$^1$ represents H or OH, R$^2$ represents N(CH$_3$)$_2$ or N—O(CH$_3$)$_2$, the line - - - represents a double or a single bond, the line . . . represents △ or a single bond, and the line ∾ represents a double or a single bond.

2. A compound according to claim 1 of the formula I, characterized in that R represents CH(OCH$_3$)$_2$, R$^1$ and R$^2$ represent acetyl, R$^3$ represents H, R$^4$ represents N(CH$_3$)$_2$, the lines - - - and . . . represent double bonds and the line ∾ represents a single bond.

3. A compound according to claim 1 of the formula I, characterized in that R represents CH(OCH$_3$)$_2$, R$^1$ and R$^3$ represent H, R$^2$ represents acetyl, R$^4$ represents N(CH$_3$)$_2$, the lines - - - and . . . represent double bonds and the line ∾ represents a single bond.

4. A compound according to claim 1 of the formula I, characterized in that R represents CH(OCH$_3$)$_2$, R$^1$, R$^2$ and R$^3$ represent H, R$^4$ represents N(CH$_3$)$_2$, the lines - - - and . . . represent double bonds and the line ∾ represents a single bond.

5. A compound according to claim 1 of the formula I, characterized in that R represents CHO, R$^1$, R$^2$ and R$^3$ represent H, R$^4$ represents N(CH$_3$)$_2$, the lines - - - and . . . represent a double bond and the line ∾ represents a single bond.

6. A compound according to claim 1 of the formula I, characterized in that R represents CH(OCH$_3$)$_2$, R$^1$ and R$^2$ represent acetyl, R$^3$ represents H, R$^4$ represents N(CH$_3$)$_2$, and the lines - - - , . . . and ∾ represent single bonds.

7. A compound according to claim 1 of the formula I, characterized in that R represents $CH(OCH_3)_2$, $R^1$ and $R^3$ represent H, $R^2$ represents acetyl, $R^4$ represents $N(CH_3)_2$, and the lines - - -, . . . and ∿ represent single bonds.

8. A compound according to claim 1 of the formula I, characterized in that R represents $CH(OCH_3)_2$, $R^1$, $R^2$ and $R^3$ represent H, $R^4$ represents $N(CH_3)_2$, and the lines - - -, . . . and ∿ represent single bonds.

9. A compound according to claim 1 of the formula I, characterized in that R represents $CH(OCH_3)_2$, $R^1$ and $R^2$ represent acetyl, $R^3$ represents H, $R^4$ represents $N—O(CH_3)_2$, the line - - - represents a double bond, the line . . . represents △ and the line ∿ represents a single bond.

10. A compound according to claim 1 of the formula I, characterized in that R represents $CH(OCH_3)_2$, $R^1$ and $R^3$ represent H, $R^2$ represents acetyl, $R^4$ represents $N—O(CH_3)_2$, the line - - - represents a double bond, the line . . . represents △ and the line ∿ represents a single bond.

11. A compound according to claim 1 of the formula I, characterized in that R represents $CH(OCH_3)_2$, $R^1$, $R^2$ and $R^3$ represent H, $R^4$ represents $N—O(CH_3)_2$, the line - - - represents a double bond, the line . . . represents △ and the line ∿ represents a single bond.

12. A compound according to claim 1 of the formula I, characterized in that R represents $CH(OCH_3)_2$, $R^1$, $R^2$ and $R^3$ represent H, $R^4$ represents $N(CH_3)_2$, the line - - - represents a single bond, the line . . . represents △ and the line ∿ represents a single bond.

13. A compound according to claim 1 of the formula I, characterized in that R represents $CH(OCH_3)_2$, $R^1$ and $R^3$ represent H, $R^2$ represents acetyl, $R^4$ represents $N(CH_3)_2$, the line - - - represents a single bond, the line . . . represents △ and the line ∿ represents a single bond.

14. A compound according to claim 1 of the formula I, characterized in that R represents $CH(OCH_3)_2$, $R^1$ and $R^2$ represent H, $R^3$ represents OH, $R^4$ represents $N(CH_3)_2$, the lines - - - and . . . represent single bonds and the line ∿ represents a double bond.

15. A compound according to claim 1 of the formula II, characterized in that R represents $CH(OCH_3)_2$, $R^1$ represents H, $R^2$ represents $N—O(CH_3)_2$, the line - - - represents a double bond, the line . . . represents △ and the line ∿ represents a single bond.

16. A compound according to claim 1 of the formula II, characterized in that R represents $CH(OCH_3)_2$, $R^1$ represents OH, $R^2$ represents $N(CH_3)_2$, the lines - - - and . . . represent single bonds and the line ∿ represents a double bond.

17. A compound according to claim 1 of the formula II, characterized in that R represents $CH(OCH_3)_2$, $R^1$ represents H, $R^2$ represents $N(CH_3)_2$, and the lines - - -, . . . and ∿ represent single bonds.

18. A compound according to claim 1 of the formula II, characterized in that R represents CHO, $R^1$ represents H, $R^2$ represents $N(CH_3)_2$, and the lines - - -, . . . and ∿ represent single bonds.

* * * * *